United States Patent
Lattuada

(10) Patent No.: US 9,506,936 B2
(45) Date of Patent: Nov. 29, 2016

(54) NON INVASIVE METHOD FOR PRENATAL DIAGNOSIS

(71) Applicant: FONDAZIONE IRCCS CA' GRANDA OSPEDALE MAGGIORE POLICLINICO, Milan (IT)

(72) Inventor: Debora Lattuada, Milan (IT)

(73) Assignee: FONDAZIONE IRCCS CA' GRANDA OSPEDALE MAGGIORE POLICLINICO (IT)

( * ) Notice: Subject to any disclaimer, the term of this patent is extended or adjusted under 35 U.S.C. 154(b) by 0 days.

(21) Appl. No.: 14/786,204

(22) PCT Filed: Apr. 24, 2014

(86) PCT No.: PCT/EP2014/058311
§ 371 (c)(1),
(2) Date: Oct. 22, 2015

(87) PCT Pub. No.: WO2014/173997
PCT Pub. Date: Oct. 30, 2014

(65) Prior Publication Data
US 2016/0069911 A1    Mar. 10, 2016

(30) Foreign Application Priority Data
Apr. 24, 2013 (IT) .............................. MI2013A0683

(51) Int. Cl.
*G01N 33/80* (2006.01)
*C12Q 1/68* (2006.01)

(52) U.S. Cl.
CPC ............. *G01N 33/80* (2013.01); *C12Q 1/6879* (2013.01); *G01N 2400/40* (2013.01); *G01N 2800/385* (2013.01)

(58) Field of Classification Search
None
See application file for complete search history.

(56) References Cited

U.S. PATENT DOCUMENTS

| 6,641,708 B1* | 11/2003 | Becker ................... B03C 5/026 204/547 |
| 6,858,439 B1* | 2/2005 | Xu ....................... B01J 19/0046 204/409 |
| 7,033,473 B2* | 4/2006 | Gascoyne ................ B03C 1/00 204/547 |
| 8,263,359 B2* | 9/2012 | Reschiglian ......... C12N 5/0663 435/29 |

OTHER PUBLICATIONS

Yang et al, Yonsei Medical Journal, 2000, vol. 41, No. 2, pp. 258-265.*
Debora Lattuada, et al. "A tag-less method for direct isolation of human umbilical vein endothelial cells by gravitation field-flow fractionation," Anal Bioanal Chem, 2013 (published online Sep. 21, 2012), 997-984, Springer-Verlag.
Mahesh Choolani, et al. "The promise of fetal cells in maternal blood." Best Practice & Research Clinical Obstetrics and Gynaecology, 2012. 655-667. vol. 26, Elsevier Ltd.
Neelima M. Bhat, et al. "One-step enrichment of nucleated red blood cells: A potential application in perinatal diagnosis," Journal of Immunological Methods, 1993, 277-280, vol. 158, Elsevier Science Publishers B.V.
International Search Report and Written Opinion for International Application No. PCT/EP2014/058311, Aug. 18, 2014, 15 pages.

* cited by examiner

*Primary Examiner* — Allison Fox
(74) *Attorney, Agent, or Firm* — Finnegan, Henderson, Farabow, Garrett & Dunner LLP

(57) ABSTRACT

The invention pertains to a method which allows separation of nucleated fetal cells, particularly fetal erythroblasts, from maternal peripheral blood. More specifically the invention relates to a non-invasive method which can isolate and provide intact nucleated fetal cells, and is useful for subsequent chromosome, gene expression and protein investigations, and is feasible at all gestational ages.

9 Claims, 11 Drawing Sheets

```
                          SEQUENCE LISTING

<160> NUMBER OF SEQ ID NOS: 2

<210> SEQ ID NO 1
<211> LENGTH: 33
<212> TYPE: DNA
<213> ORGANISM: Homo sapiens
<220> FEATURE:
<221> NAME/KEY: source
<222> LOCATION: 1..33
<223> OTHER INFORMATION: /organism="Homo sapiens"
      /note="Hemophilia heterozygosity"
      /mol_type="unassigned DNA"

<400> SEQUENCE: 1
ctaccttcga attcaccccc agagttgggt gca                               33

<210> SEQ ID NO 2
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /organism="Homo sapiens"
      /note="Hemophilia homozygosity"
      /mol_type="unassigned DNA"

<400> SEQUENCE: 2
taccttcgaa ttcaccccca gagttgggtg                                   30
```

NON INVASIVE METHOD FOR PRENATAL DIAGNOSIS

CROSS-REFERENCE TO RELATED PATENT APPLICATIONS

This application is a National Stage Entry under 35 U.S.C. §371 of International Application No. PCT/EP2014/058311, filed Apr. 24, 2014, which claims priority to IT Application No. MI2013A000683, filed Apr. 24, 2013.

FIELD OF THE INVENTION

The invention relates to a method for isolating fetal nucleated cells, particularly fetal erythroblasts ("Nucleated Red Blood Cells", NRBC) from maternal peripheral blood. More specifically, the invention relates to a non-invasive method enabling isolation and provision of intact fetal nucleated cells, which are useful for further investigations on chromosomes, gene and protein expression for prenatal diagnosis feasible in all gestational ages.

STATE OF THE ART

Prenatal diagnosis of chromosomal abnormalities and genetic diseases necessarily requires a source of fetal DNA or chromosomes.

Chromosomal abnormalities affect 9 out of 1,000 live births, with a higher incidence with advanced maternal age (1/80 for mothers that have reached 40 years of age).

By contrast, with respect to genetic abnormalities, research is in continuous development and there is an increasing number of identifiable diseases, such as cystic fibrosis, sickle cell anemia and Duchenne syndrome. With the advances in genomic sequence information, the number of these genetic diseases is expected to grow substantially. Their relative incidence also varies according to particular phenotypic strains and geographical areas.

Non-invasive or invasive prenatal screening tests are already established in order to identify possible chromosomal abnormalities and genetic diseases.

Non-invasive analysis known to date consist of tests based on morphological (eg. nuchal translucency ultrasound) and hematochemical (Bi-test and Tri-test on maternal blood) analyses not involving any risk for the mother and the child, however with a relevant degree of approximation (so-called "operator-dependent"). Unfortunately the non-invasive analysis known to date bear the disadvantage of being unable to provide a clear and safe outcome, and do not allow clear identification of a dysfunction. Only a preliminary investigation is made possible by these analyses.

Instead the invasive tests make possible to analyze chromosomal or genetic abnormalities based on analysis of fetal DNA. They consist of diagnostic tests involving a significant risk for the fetus, such as amniocentesis and villocentesis. Amniocentesis involves sampling of amniotic fluid containing fetal cells which can be cultured. Such a technique is known since the 50's and is freely offered to pregnant women starting from the 35$^{th}$ year of age or under particular risk conditions.

Chorionic villus sampling (villocentesis) involves collection of villi from the gestational chamber.

This technique is known since the late 60's and is proposed as (less common) alternative to amniocentesis.

Both these invasive tests involve significant risks of compromising the proper course of pregnancy with a prevalence that exceeds 1% and wide variations depending on the setting where they are performed.

The observation that fetal DNA is present in maternal blood dates back to 1997 (Lo Y M D, et al. Presence of fetal DNA in maternal plasma and serum. Lancet 1997; 350:485 e7) and many groups around the world are since working on development of an effective method for prenatal diagnosis and early identification of major genomic and chromosomal abnormalities in the fetus.

To date, however, the analysis of fetal DNA only makes possible to determine the sex of the fetus and the RhD factor, while a protocol for trisomy 21 was developed in 2010 (Chiu R W K e Lo Y M D Non-invasive prenatal diagnosis by fetal nucleic acid analysis in maternal plasma: the coming of age. Seminars in Fetal & Neonatal Medicine xxx (2010) 1e6).

However, there are at least two major problems with the use of fetal DNA in maternal blood. The first problem is to isolate and identify with certainty free circulating fetal DNA from maternal DNA, the second problem is the reliability of isolated DNA, due to the fact that fetal DNA is fragmented.

Nowadays there is still a need for novel noninvasive diagnostic techniques allowing proper and accurate diagnosis of fetal chromosomal abnormalities and genetic disorders in different gestational ages, which are devoid of risks for the fetus or the mother and at the same time reproducible and advantageous from practical and economical points of view.

One of the objectives of the present invention is to provide a method to isolate nucleated fetal cells, particularly erythroblasts containing intact DNA, from the other cells present in maternal blood.

Therefore another objective of the present invention is to provide a suitable method for rapid and early diagnosis of fetal chromosomal abnormalities and genetic diseases by use of a non-invasive procedure, thus providing precise and safe indications without risks and without the above mentioned disadvantages of the known non-invasive and invasive methods.

SUMMARY OF THE INVENTION

Therefore the invention relates to a method for isolation of intact fetal erythroblasts from a sample of peripheral blood of a pregnant woman comprising the steps of:
a. applying a laminar flow by gravitational field-flow fractionation (GrFFF) to a blood sample containing isolated intact fetal erythroblasts; and
b. isolating intact fetal erythroblasts from the other blood components.

Another aspect the invention relates to a diagnostic kit for the isolation of intact fetal erythroblasts from maternal peripheral blood according to the method of the present invention, comprising:
 a solution for the preparation of density gradients,
 a saline solution for dilution of peripheral blood sample,
 heparin; and optionally washing solution.

DESCRIPTION OF THE FIGURES

The invention will now be described in detail and with reference to the attached Figures, wherein.

DETAILED DESCRIPTION OF THE INVENTION

Figure 1:
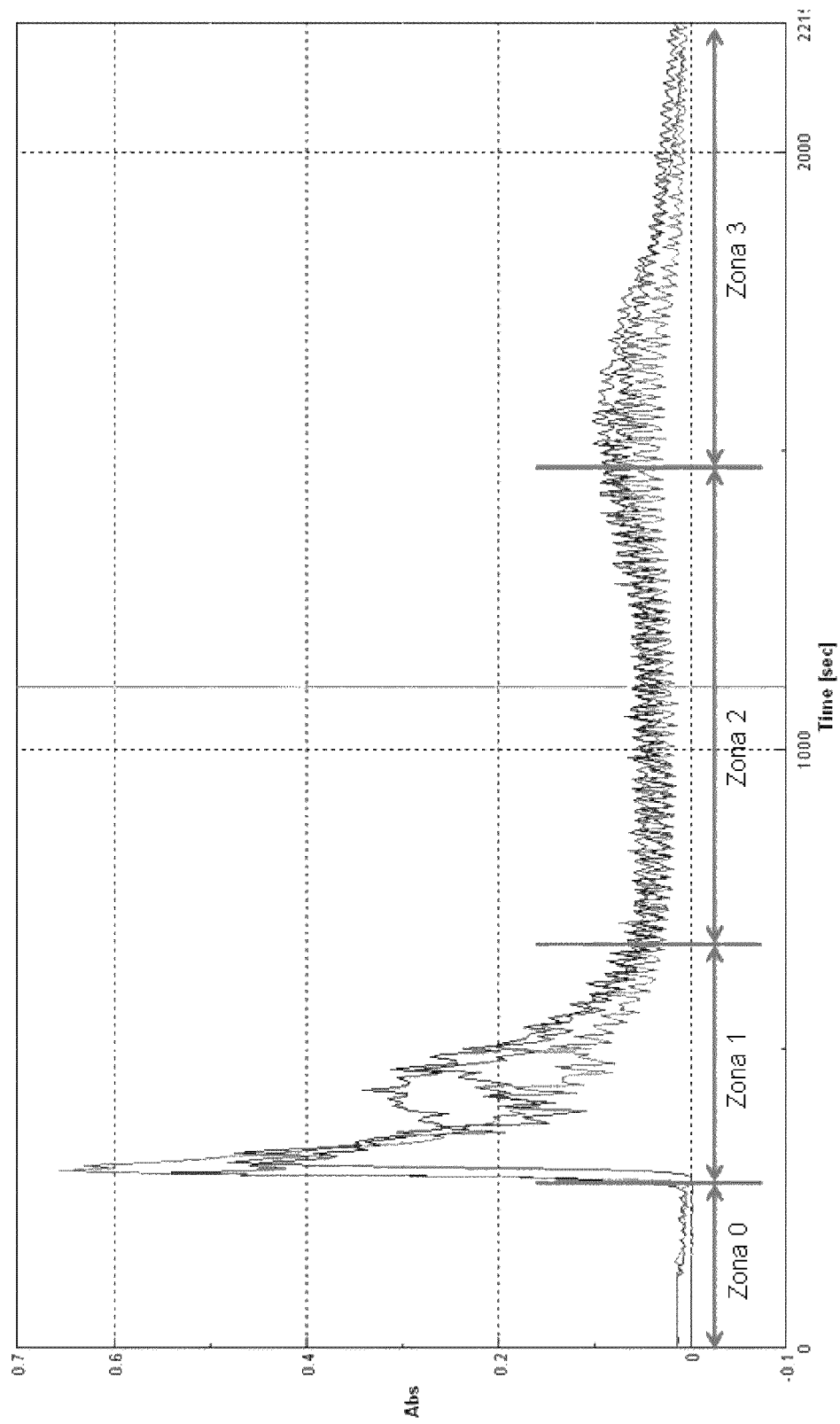
FIG. 1: shows a representative fractogram of a GrFFF separation from example 4, the graph is generated from the 600 nm absorption spectrum relative to the separation time of the blood cells of a pregnant woman at 9 weeks of gestation, separated by Lympholite. Mobile phase: saline supplemented with heparin. Relaxation time 2'. Elution rate: 0.25 ml/min. Number of injected cells: $5 \times 10^5$. Fraction collection: 1000-1500 sec. The three lines represent three different runs of the same sample. Four zones can be inferred from the absorption spectrum: zone 0, wherein flow stability is controlled; zone 1, also termed Void, wherein increased absorbance is detected with the outflow of cell debris and lymphocytes; zone 2 wherein absorbance decreases without returning to the 0 value; zone 3 wherein absorbance increases with the outflow of lymphocytes and granulocytes.

Therefore the invention relates to a method for isolation of intact fetal erythroblasts from a sample of peripheral blood, in particular of a pregnant woman, comprising the steps of:

a. applying a laminar flow through by gravitational field-flow fractionation (GrFFF) to a blood sample containing isolated intact fetal erythroblasts; and b. isolating the intact fetal erythroblasts from other blood components.

In the present invention, the definition:
"laminar flow by gravitational field-flow fractionation (GrFFF) system" refers to a technique that allows separation of cells with different sizes and morphologies. The sample is introduced into a channel designed to allow application of a laminar flow which physically separates and allows isolation of its various components.

The method according to the present invention may comprises an additional step c, of extracting DNA, RNA and proteins from fetal erythroblasts isolated in step b. DNA and RNA extraction can be performed by different experimental protocols. Regardless of the extraction technique used, this should meet two main requirements: yield and purity, meant as both presence in solution of the nucleic acid under examination and absence of contaminants which can bind the reagents in solution and alter the results of sequencing.

The extraction and purification process typically involves the following four steps: cell lysis, inactivation of cellular nucleases, separation and recovery of nucleic acid from the solution containing the cell lysate and precipitation.

Protein extraction can be carried out through different experimental protocols.

In one embodiment, the method according to the present invention is a diagnostic method.

In a preferred embodiment, according to the method of the present invention, the sample of peripheral blood is treated with a solution for preparation of density gradients before applying the laminar flow to the sample.

Ficoll is an example of solution for preparation of density gradients. Ficoll is a very high molecular weight, water-soluble, synthetic branched copolymer, synthesized from sucrose and epichlorohydrin, which is used to prepare density gradients for cell separation.

In the method according to the present invention, the sample of peripheral blood is advantageously taken from the eighth to the twenty-second week of gestation.

In some embodiments of the method of the present invention, the laminar flow applied to the blood sample containing intact fetal erythroblasts is a flow with a rate ranging from about 100 µl/min to about 1 ml/min, such as a flow rate of 250 µl/min.

In some embodiments the method according to the present invention involves a laminar flow in which said laminar flow is applied to a sample having a concentration ranging from about $1\times10^5$ to $1\times10^6$ cells in 50 µl, such as approximately $5\times10^5$ cells in 50 µl.

According to other embodiments of the method according to the present invention, said fetal erythroblasts are isolated at an elution time ranging from 5 minutes to 40 minutes.

In one embodiment of the method of the present invention, said isolated fetal erythroblasts are used to carry out a prenatal diagnosis allowing detection of possible chromosomal abnormalities and genetic diseases.

In a preferred embodiment, in the method according to the present invention, said chromosomal abnormalities are numerical abnormalities or structural abnormalities of chromosomes and said genetic diseases are selected from the group consisting of cystic fibrosis, sickle cell anemia, hemophilia, Duchenne muscular dystrophy, spinal amyotrophy and neurofibromatosis.

As a result of mutations, the karyotype may change with respect to number or morphology of chromosomes that constitute it, respectively giving rise to numerical abnormalities of chromosomes (aneuploidy) and to structural abnormalities of chromosomes.

The most frequent numerical aneuploidies observed in humans are monosomy (absence of one element of the pair of homologous chromosomes) and trisomy (presence of one additional element of the pair of homologous chromosomes). These instances are defined as complete monosomy and trisomy, however partial monosomy/trisomy can also occur due to the absence or to the presence in triple copy of individual chromosome segments.

Complete monosomies are incompatible with postnatal life, except X chromosome monosomy associated with Turner syndrome (45,X).

On the contrary, complete trisomies of some chromosomes, such as trisomy 21 or Down syndrome (47,XX,+21), trisomy 18 or Edwards syndrome (47,XX,+18), trisomy 13 or Patau syndrome (47,XX,+13) are compatible with postnatal life, as well as sex chromosome aneuploidies.

Genetic diseases can be mono- or multi-factorial.

Monofactorial genetic diseases are caused by mutation of a single gene and are also termed mendelian. So far, researchers have categorized about 7000 of these diseases. The best known are cystic fibrosis, Duchenne muscular dystrophy, spinal amyotrophy, and neurofibromatosis.

Multifactorial genetic diseases result from the combination of several concurring genetic and environmental factors. In general, multifactorial diseases typically include the most common pathologies of adulthood such as asthma, osteoporosis, obesity, hypertension, coronary heart disease along with various cardiac malformations. Both in the neonatal period and older ages, the clinical impact of these diseases represents a substantial burden.

In another aspect, the invention relates to a diagnostic kit for isolation of intact fetal erythroblasts from maternal peripheral blood according to the method of the present invention, comprising:

a solution for the preparation of density gradients,
a saline solution for dilution of the peripheral blood sample,
heparin and optionally washing solutions.

For illustrative purpose, examples of embodiments of the present invention are provided below.

EXAMPLES

Example 1

Patients

Pregnant women were recruited at the obstetrics department of the Clinica Mangiagalli, after they provided the informed consent. Six to 14 ml of venous blood were collected from 130 pregnant women (Table 1).

TABLE 1

Table 1. List of patients analysed, divided by their number according to gestational age.

| Weeks of gestation | No. of patients |
|---|---|
| 5 | 1 |
| 6 | 3 |
| 8 | 1 |
| 9 | 5 |
| 10 | 5 |
| 11 | 15 |
| 12 | 25 |
| 13 | 10 |
| 14 | 7 |
| 15 | 15 |
| 16 | 17 |
| 17 | 5 |
| 18 | 5 |
| 20 | 2 |
| 21 | 3 |
| 23 | 1 |
| 24 | 2 |
| 25 | 1 |
| 28 | 4 |
| 30 | 1 |
| 35 | 1 |

Gestational age when it is possible to identify NRBC ("Nucleated Red Blood Cells"): samples from 5 to 35 weeks of gestation were analysed. There is an intra-subject variability, however, as described in the literature, the largest amount of NRBC was found in the early weeks of gestation. The optimal collection period is around 8-12 weeks of gestation.

Example 2

Sample Pretreatment by Isolation of Nucleated Cells

The NRBC isolation step is preceded by a step of pretreatment of the maternal peripheral blood sample prior to separation.

The pretreatment step can be advantageously carried out for example by means of a solution for preparation of density gradients such as Ficoll or through Lympholite-H (Euroclone, Milan).

Other types of sample pretreatment can be anticipated, as for instance the lysis or the dilution of erythroblasts.

Example 3

Sample Loading into the Channel

The sample pretreated and separated as described in Example 2 is loaded into the channel of the instrument for cell separation by GrFFF.

Before sample loading, the channel is washed with 20% sodium hypochlorite solution and then extensively washed with sterile distilled water and finally washed with heparin-containing sterile saline. When the flow within the channel is stable (=stable absorbance), the pretreated sample is injected into the channel.

Approximately $5 \times 10^5$ cells in 50 µl final volume are loaded into the channel.

Relevant parameters for a good separation of the sample in the channel are:
sample dilution factor;
number of cells loaded into the channel;

variability of the relaxation period of the cells within the channel;

flow rate within the channel; and characteristics of the dilution medium and of the anticoagulant factors present.

Regarding the sample dilution factor, it can vary in a range from approximately $1\times10^5$ to $1\times10^6$ cells in 50 µl, such as approximately $5\times10^6$ cells in 50 µl.

Regarding the number of cells to be loaded into the channel, poor sample separation has been observed in the case of loading of too few cells (exceedingly diluted sample) or of too many cells (exceedingly concentrated sample).

The relaxation period lasts about two minutes, and no significant improvement is found with longer periods of 4 or 6 minutes, whereas a shorter period results in poor separation.

Regarding the elution medium, the best results were obtained with saline supplemented with heparin 1:1000, employing EPSOCLAR Heparin 25,000 IU/5 ml, solution for infusion.

The flow rate within the channel can vary in a range from about 50 µl per minute up to 1 ml per minute, rate such as in a range from about 100 µl/min to about 400 µl/min, or at the rate is 250 µl/min.

Example 4

Sample Analysis by Absorbance

Figure 2:
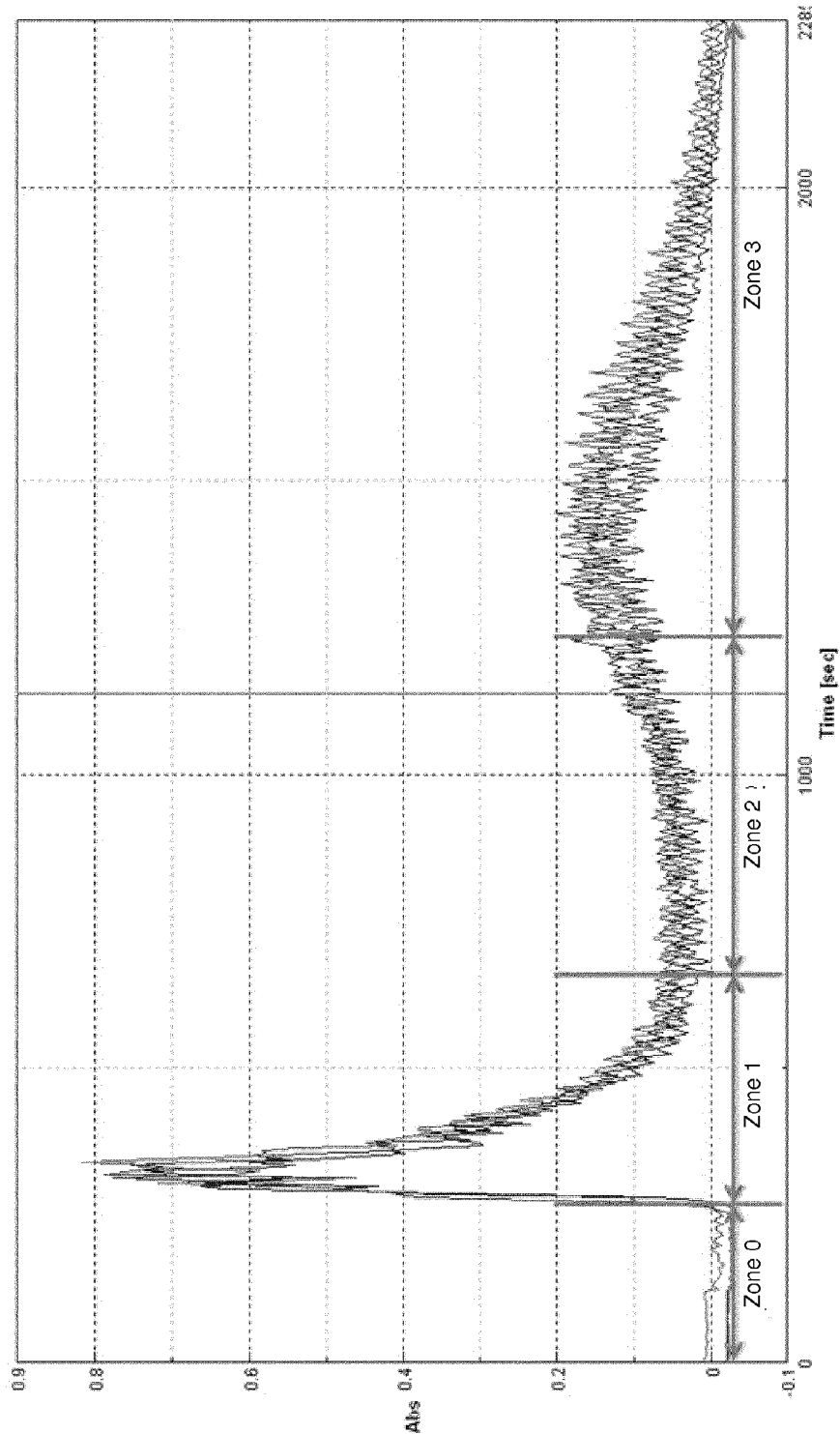
FIG. 2 shows a representative fractogram of a GrFFF separation from example 4, the graph generated from the 600 nm absorption spectrum relative to the separation time of the blood cells of a pregnant woman at 18 weeks of gestation, separated by Lympholite, where the Mobile Phase is: saline supplemented with heparin. Relaxation time 2'. Elution rate: 0.3 ml/min. Number of injected cells: $6\times10^5$. Fraction collection: 950-1250 sec. Green, red and blue lines represent three different runs of the same sample. Four zones can be inferred from the absorption spectrum: zone 0, wherein flow stability is controlled; zone 1, also termed Void, wherein increased absorbance is detected with the outflow of cell debris and lymphocytes; zone 2 wherein absorbance decreases without returning to 0 value; zone 3 wherein absorbance increases with the outflow of lymphocytes and granulocytes.

The sample separated in the channel as described in example 3 is read by a spectrophotometer at 600 nm, producing a graph as exemplified for samples of FIG. 1 and FIG. 2.

In the graph, three zones can be distinguished that show a change in absorbance with respect to the zero value obtained in the runs of saline solution with heparin (zone 0):

zone 1 (void) corresponds to the outflow from the channel of cellular debris and lymphocytes;

zone 2 corresponds mainly to the outflow of fetal nucleated cells;

zone 3 corresponds mainly to the outflow of granulocytes.

Example 5

Characterization of Fractions of Harvested Cells

Cells in each fraction were counted with a Burker chamber and were plated onto glass slides by "smear" or cytospin.

Figure 3:
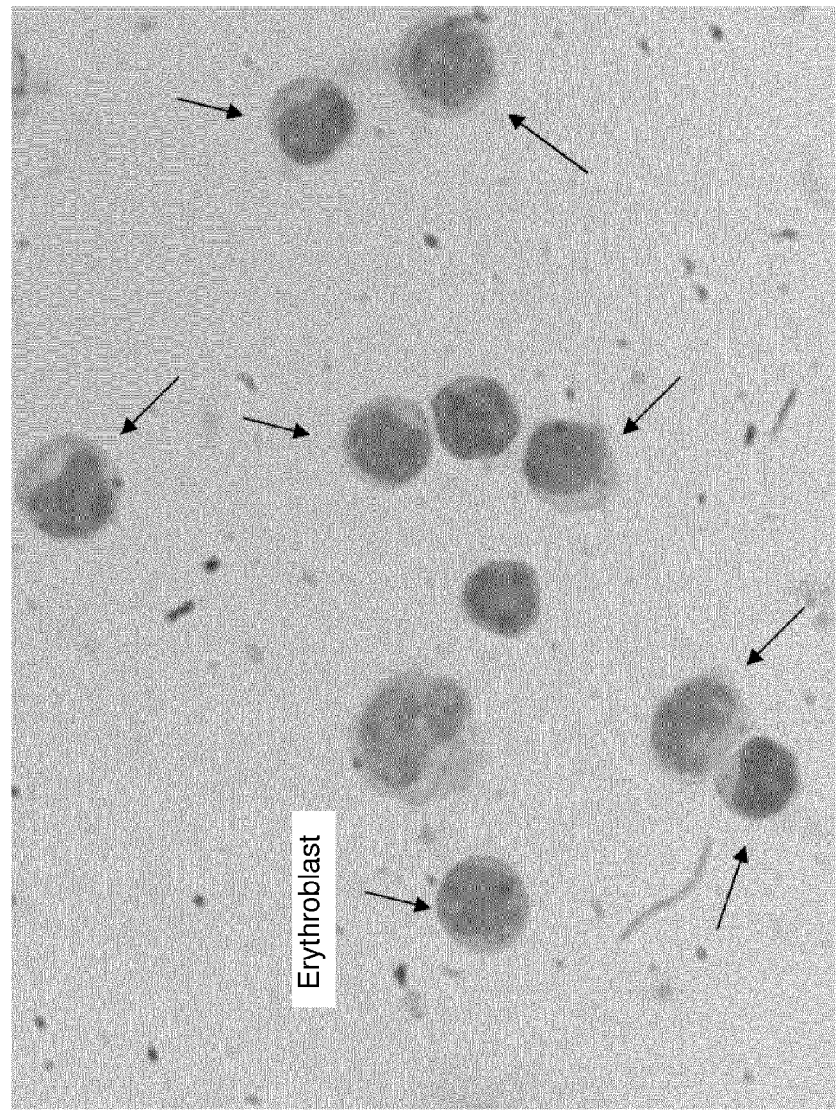
FIG. 3 shows a microscopy image from example 5 of erythroblasts fixed on glass slide by cytospin and stained with Giemsa, 100× magnification.
Figure 4:
FIG. 4 shows a microscopy image from Example 5 of erythroblasts fixed on glass slides by cytospin and stained with Ortho-Dianisidine, 100× magnification.

Cells were subsequently stained with Giemsa (FIG. 3) and with O-Dianisidine (FIG. 4) and analyzed by microscopy in order to verify NRBC presence.

It was possible to detect the presence of erythroblasts (NRBC) in the eluate fraction collected.

Example 6

FACS Analysis

FACS analysis was carried out on 12 patients.

The Gravitational field-flow fractionation (GrFFF) system has proven capable of separating the different types of populations present in maternal blood.

Figure 5:
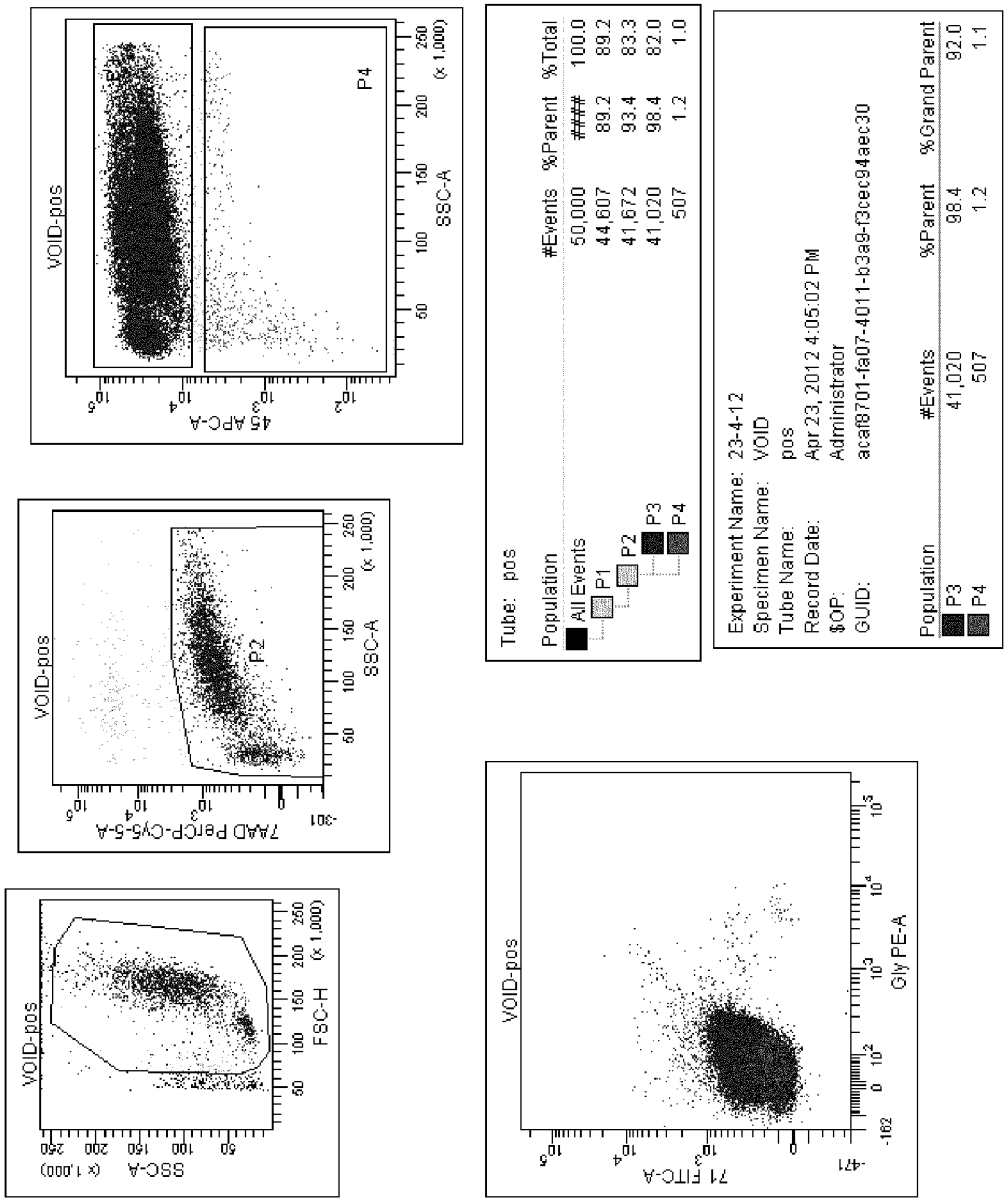
FIG. 5 shows a representative example of cytofluorimetric analysis from example 6. Cells can be divided in distinct populations: P1, P2, P3 and P4. P1 are all cells, P2 are live cells (7AAD-PE vs SSC), P3 are CD45+ cells (CD45-PE vs SSC), P4 are CD45− cells (CD45-PE vs SSC). It can be inferred from the lower left panel which cells of group P3 and P4 test positive or negative for Glycophorin (Gly) and for CD71 (Gly-PE vs 71-FITC-A). Panel A, B and C show maternal blood cells separated by Lympholite and collected from the ring. In particular, panel A shows the analysis of cells separated in zone 1, termed VOID; panel B shows the analysis of cells separated in zone 2, termed plate; panel C shows the analysis of cells separated in zone 3, termed peak. Box D shows the FACS analysis of cells sedimented at the bottom of the tube during Lympholite separation, after hypo-osmotic reaction, termed pellet.
Figure 5:
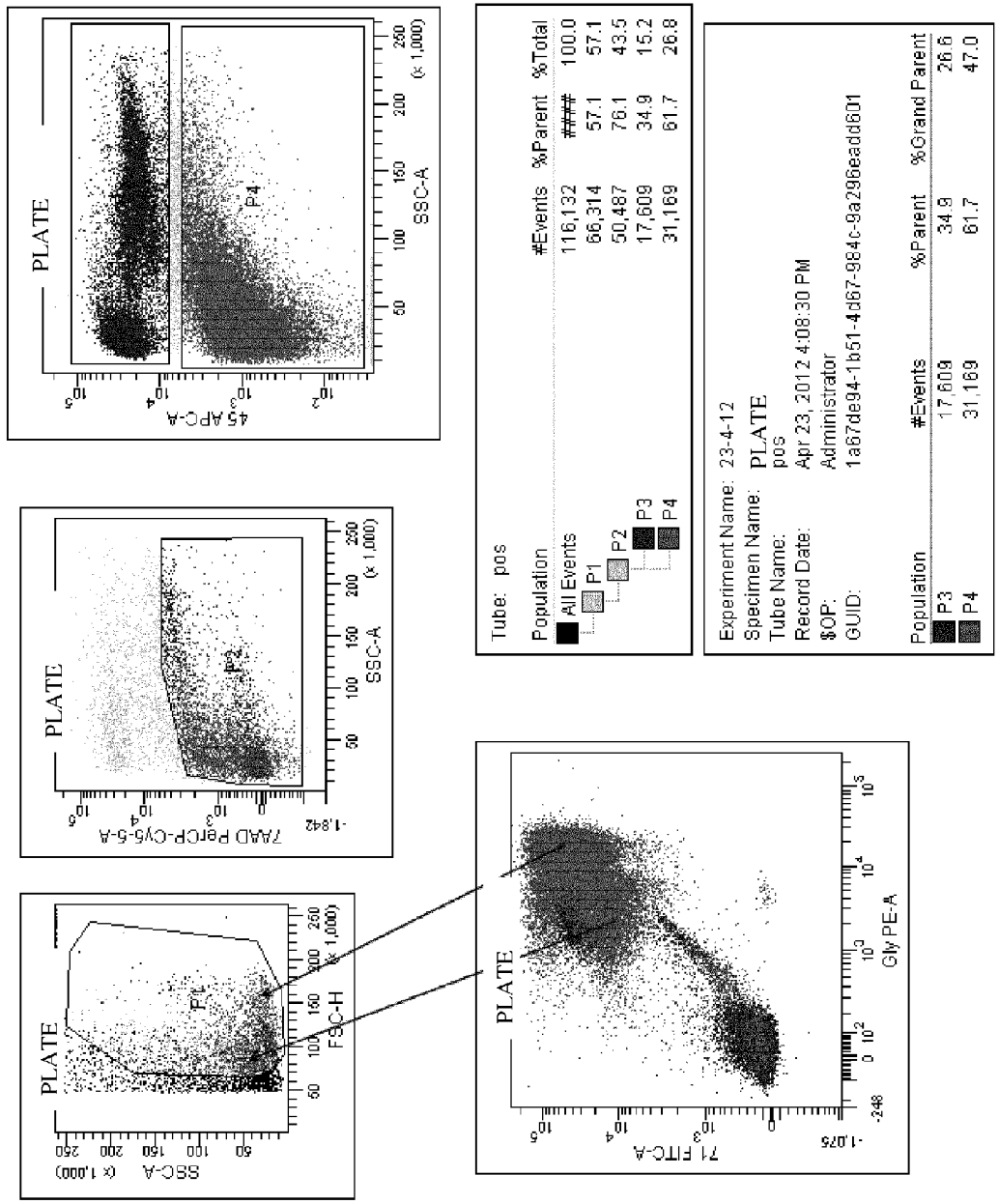
Figure 5:
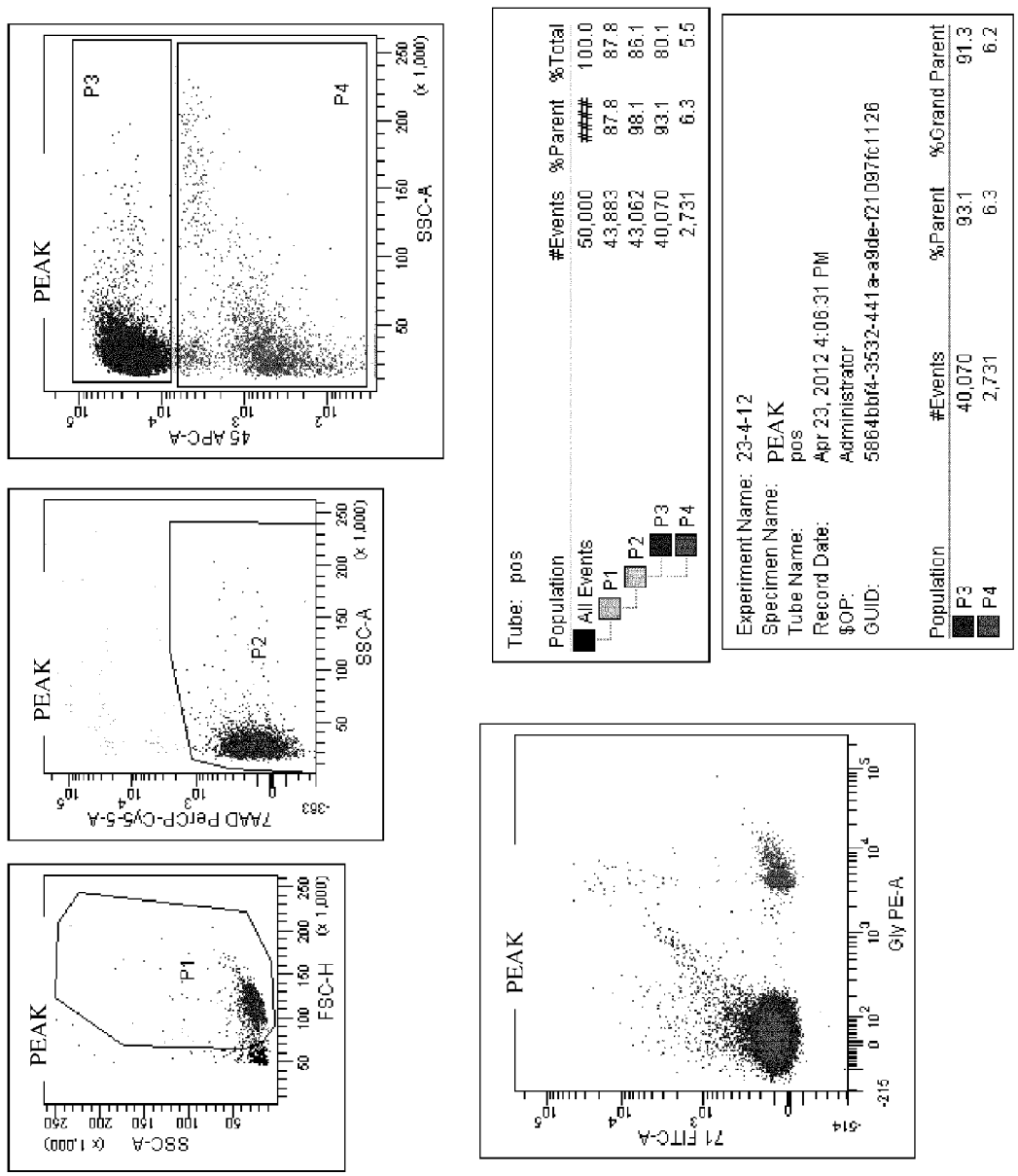
Figure 5:
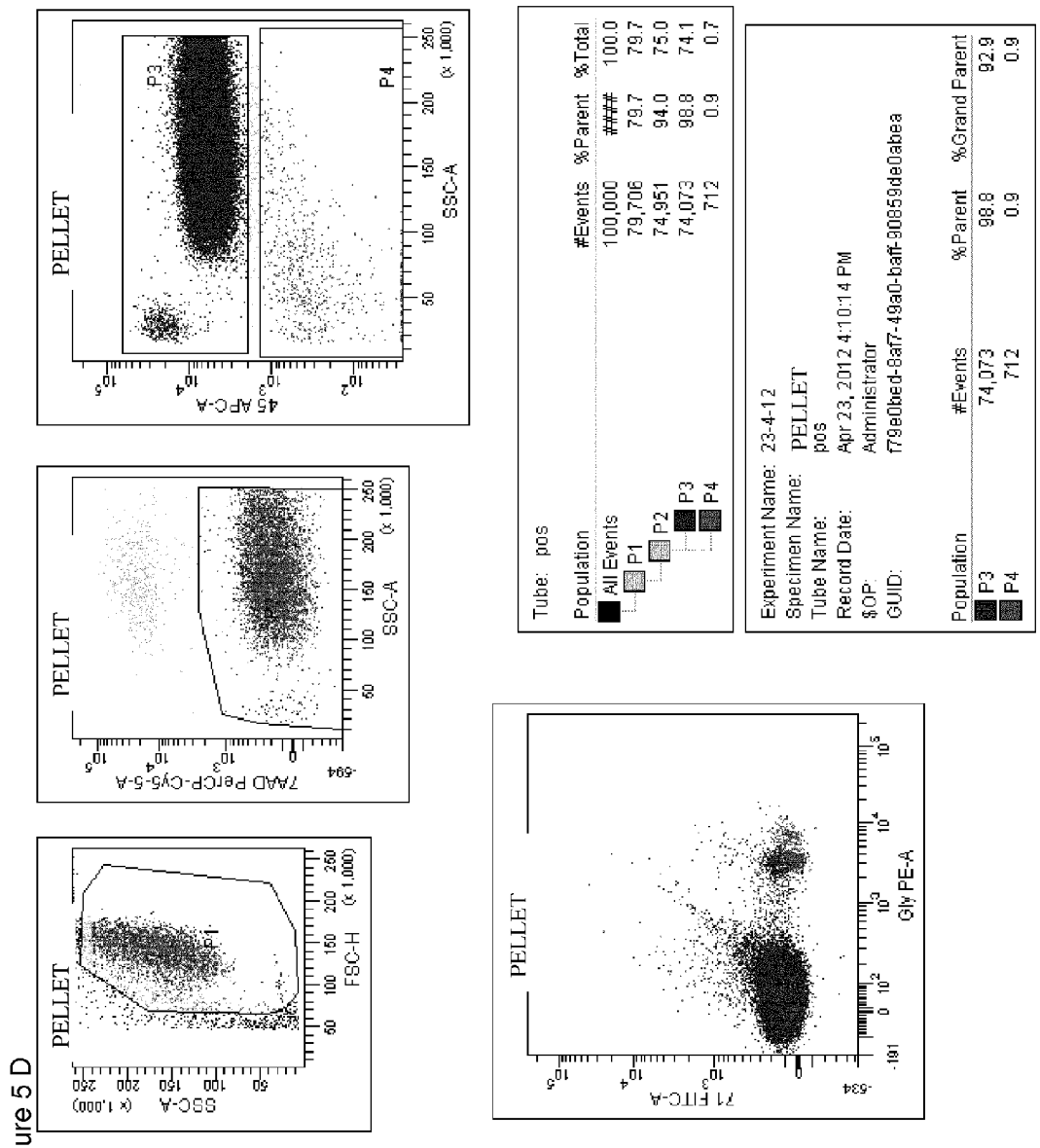

Fetal erythroblasts ("Nucleated Red Blood Cells", NRBC) are found in zone 2 (FIG. 5).

The percent yield of NRBC has reached even 61.7% of live cells and further enrichment is conceivable by negative selection of $CD45^+$ cells since NRBC are CD45−. In this case the yield would be around 100%.

Example 7

Real-Time PCR and QF PCR Analysis

Figure 6:
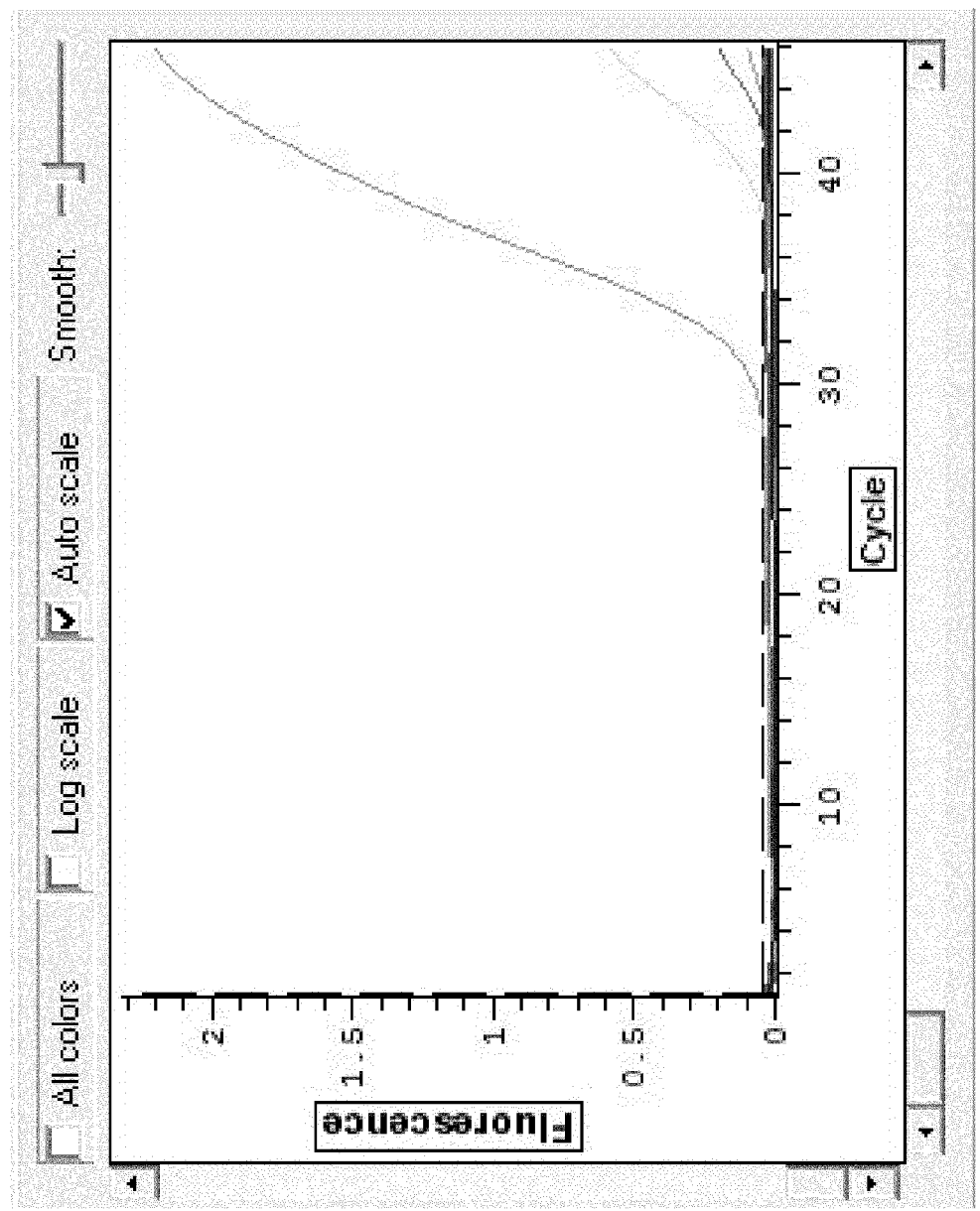
FIG. 6 shows an image of Real-Time PCR analysis from example 7 on samples of fetal cells separated from maternal blood by use of GrFFF, and collected in zone 2. An increase in fluorescence can be observed in three samples, indicating the presence of the Y chromosome. The fluorescence increases also in the positive control for the male subject, while does not change for the female subject.

To find out if it was possible to identify the sex of the fetus from fetal cells isolated as described in example 3, real-time PCR analysis was conducted on 11 samples by using a Y-specific probe detecting the presence of the SRY gene; using a SRY probe (Y. M. Dennis Lo, Mark S. C. Tein, Tze K. Lau, Christopher J. Haines, Tse N. Leung, Priscilla M. K. Poon, James S. Wainscoat, Philip J. Johnson, Allan M. Z. Chang, and N. Magnus Hjelm Quantitative Analysis of Fetal DNA in Maternal Plasma and Serum: Implications for Noninvasive Prenatal Diagnosis Am. J. Hum. Genet. 62:768-775, 1998) it was possible to determine the presence of the SRY gene and therefore the presence of the Y chromosome in male samples. In particular the above described experiment is shown in FIG. 6, where it can be observed in samples from males an increase in fluorescence which is not detected in control samples from females.

Also QF-PCR ("Quantitative Fluorescence-PCR") analysis on one sample showed the presence of two different genomes, i.e. maternal DNA and fetal DNA.

Figure 7:
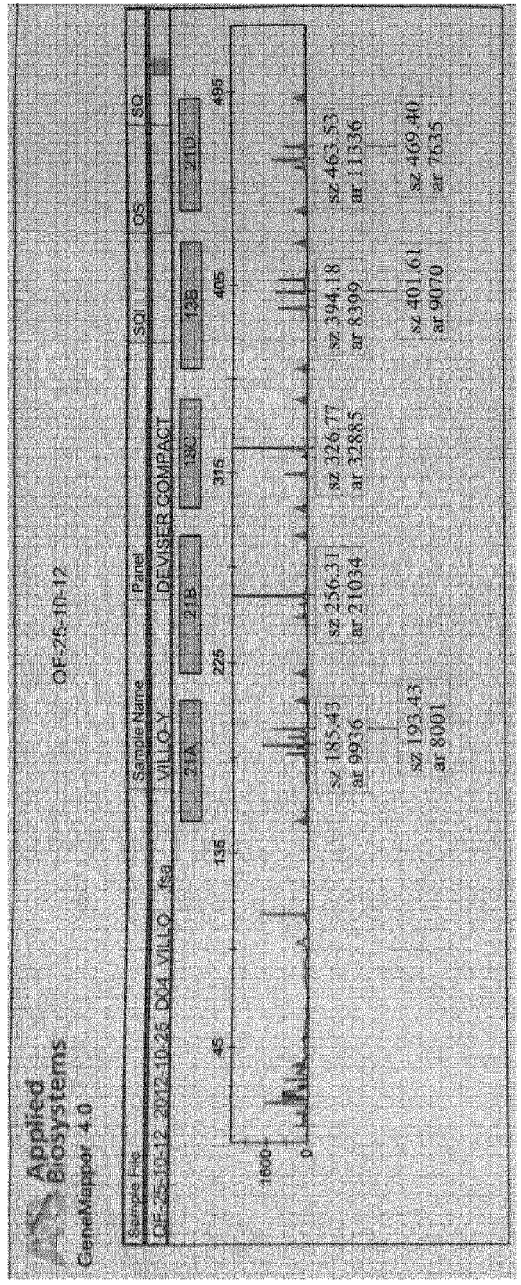
FIG. 7 shows the analysis of a sample from example 7, done with cells harvested in zone 2 by QF-PCR ("Quantitative Fluorescence— PCR"); it shows the presence of two different genomes, i.e. the presence of maternal DNA and fetal DNA. In particular, it is possible to infer the presence of different peaks with respect to both height and number (three or even four peaks) which provide the indication that two different genomes are present.
Figure 8:
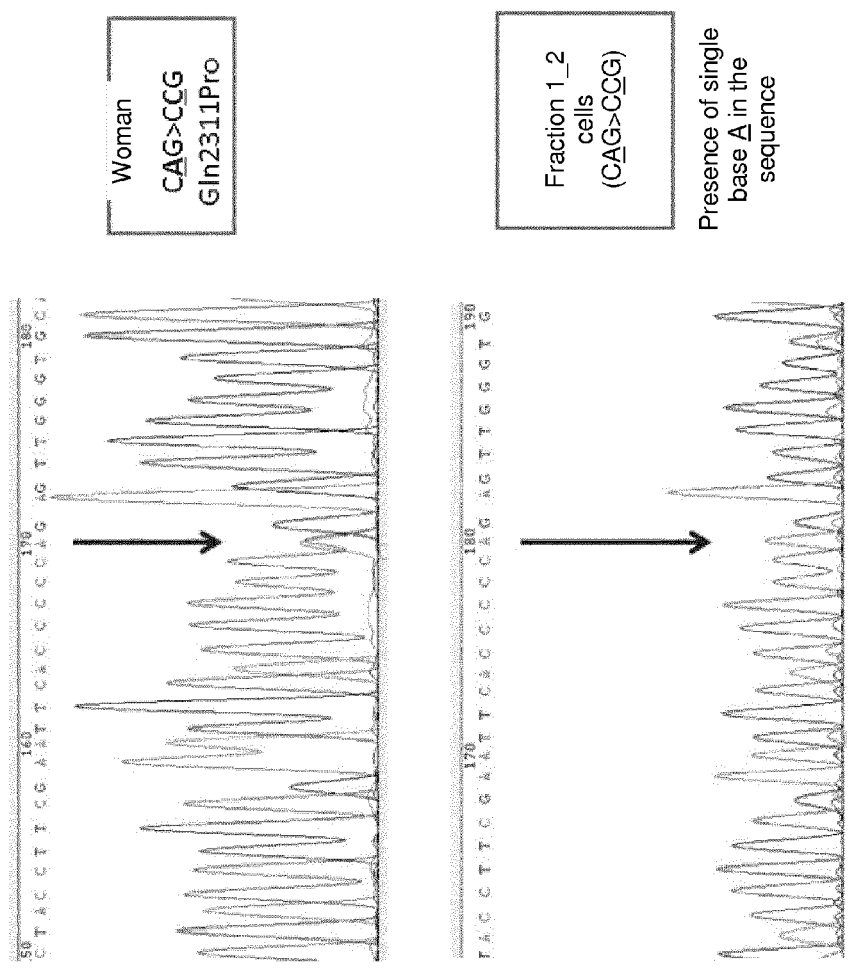
FIG. 8 shows an analysis from example 8 of the sequence of the DNA extracted from a blood sample from a pregnant woman carrying hemophilia. Blood from the pregnant women was processed by Lympholite, nucleated cells were separated by GrFFF, and a very small fraction of the final part of zone 2 was collected. The sequence shows the presence of heterozygosity in the DNA of the pregnant woman (presence of base A and C) and of homozygosity in the fetal cells (presence of single base A) separated by GrFFF.

In particular, FIG. 7 shows the presence of different peaks with respect to both height and number (three or even four peaks), thus providing the indication that two different genomes are present.

Example 8

Sequencing of DNA from Fetal Cells from a Pregnant Woman Carrying Hemophilia

Sequencing analysis of the disease gene region was possible in a single hemophilic patient. The mother was found to be heterozygous and the fetus was found to be homozygous.

Example 9

Example of Operational Protocol

Remove Lympholite from the refrigerator at least 20' in advance to equilibrate it at room temperature (in order to obtain the proper density for cell separation).

Remove the PBS from the refrigerator at least 20' in advance to equilibrate it at room temperature (in order to prevent a thermal shock for the cells).

Switch on the peristaltic pump to stabilize the flow in the channel. Rate 0.35 ml/min.

1. Test tube containing Blood sample and EDTA (14 ml) is diluted with the same volume of PBS (not cold).
2. Aliquot a volume of Lympholite equal to the blood volume into falcon tubes (Room Temperature).
3. Pour very gently the PBS-diluted blood on the wall of the test tube without breaking the Lympholite interface.
4. Centrifuge at 800×g for 26 minutes with 0 brake.
5. Recover the lymphocyte ring with a glass pasteur pipette.
6. Add saline solution+heparin (1:1000) and centrifuge at 800×g for 10 minutes.
7. Add saline solution+heparin (1:1000) to the pellet.
8. Resuspend pellet in 400 microliters of saline solution+heparin (1:1000).

9. Count cells:
   prepare the Burker chamber, adapting the cover glass in order to cover both counting chambers;
   prepare a 1:20 solution by adding 1 μl of cell suspension to 19 μl of saline solution+Heparin (or more accurately 2 μl of cell suspension to 38 μl of saline solution+Heparin) in a new tube;
   prepare a second test tube and add 1 μl of trypan blue to 9 μl of the previous 1:20 dilution;
   load in a Burker chamber by capillarity 10 μl of the sample of the second test tube (consisting of 1 μl of trypan blue and 9 μl of the previous 1:20 dilution);
   Wait a few seconds for the cells to pause in the fields and count 4 large squares: count only live cells (those in which the dye has not penetrated);
   calculate the mean (M), multiply by the dilution factor (20) and $10^4$ (the Barker chamber factor): M×20× $10^4$=no cells per ml;
   multiply the volume of cells per ml by the volume of suspension (0.4 ml): cells per ml×0.4=total cells present in the suspension.
10. Load 5-6×$10^5$ cells as 50 μl of cell suspension, calculating the necessary dilution factor of the suspension.
11. Stop the flow. Inject the sample with a syringe.
12. Restart the flow at 0.25 ml/min for 15".
13. Stop and let relax the sample for 2'.
14. Turn the valve.
15. Restart the flow at 0.35 ml/min.
16. Collect the first part of the peak (from flat to plateau) in a falcon tube.
17. Before the second injection, allow the sample to completely outflow from the channel.
18. Once several fractions of the first part of the peak have been collected, centrifuge at 800×g for 6'.
19. Dry pellets for subsequent DNA extraction or resuspend the pellet for counting and plating in the slide.

The advantages achieved by the method of the present invention are evident from the detailed description and from the above Examples. In particular, this method has proved surprisingly and advantageously suitable for non-invasive diagnosis of chromosomal abnormalities and genetic diseases of the fetus. At the same time, this method, being fast and extremely easy to perform, can be conveniently applied in any type of research or diagnostic analysis laboratory.

The invention claimed is:

1. A method for isolating intact fetal erythroblasts from a sample of peripheral blood of a pregnant woman comprising the steps of:
   applying a laminar flow by gravitational field-flow fractionation (GrFFF) to the blood sample containing isolated intact fetal erythroblasts, and
   isolating the intact fetal erythroblasts from other blood components.

2. The method according to claim 1, comprising the further step of:
   extracting DNA, RNA, and proteins from the isolated intact fetal erythroblasts.

3. The method according to claim 1, wherein before applying the laminar flow, the blood sample is treated with a solution for preparing density gradients.

4. The method according to claim 1, in which the peripheral blood sample derives from a pregnant female from an eighth to a twenty-second week of gestation.

5. The method according to claim 1, in which the laminar flow is applied at a velocity which ranges from about 50 to about 1 ml/min.

6. The method according to claim 1, in which the laminar flow is applied to a sample which ranges from about 1×$10^5$ cells to 1×$10^6$ cells in 50 μl.

7. The method according to claim 1, in which said isolated fetal erythroblasts are isolated at an elution time which ranges from 5 minutes to 40 minutes.

8. The method according to claim 1, in which said isolated fetal erythroblasts are used to make a prenatal diagnosis that allows an identification of any chromosomal abnormalities and genetic diseases.

9. The method according to claim 8, wherein said chromosomal abnormalities are numerical or structural abnormalities of the chromosomes, and said genetic disorders are selected from a group consisting of cystic fibrosis, sickle cell anemia, hemophilia, Duchenne muscular dystrophy, spinal amyotrophy, and neurofibromatosis.

* * * * *

UNITED STATES PATENT AND TRADEMARK OFFICE
CERTIFICATE OF CORRECTION

PATENT NO. : 9,506,936 B2  
APPLICATION NO. : 14/786204  
DATED : November 29, 2016  
INVENTOR(S) : Lattuada Page 1 of 1

It is certified that error appears in the above-identified patent and that said Letters Patent is hereby corrected as shown below:

On the Title Page

Item (57), Line 7, "feasible at ail gestational ages" should read -- feasible at all gestational ages --.

In the Claims

Claim 5, Column 10, Lines 63-64, "from about 50 to about 1 ml/min." should read -- from about 50 µl to about 1 ml/min. --.

Signed and Sealed this  
Twenty-fifth Day of April, 2017

Michelle K. Lee  
*Director of the United States Patent and Trademark Office*